US00PP14943P2

(12) United States Plant Patent
Austin

(10) Patent No.: US PP14,943 P2
(45) Date of Patent: Jun. 22, 2004

(54) SHRUB ROSE PLANT NAMED 'AUSJUMP'

(50) Latin Name: *Rose hybrida*
Varietal Denomination: AUSjump

(75) Inventor: David C. H. Austin, Albrighton (GB)

(73) Assignee: David Austin Roses Limited, Albrighton (GB)

( * ) Notice: Subject to any disclaimer, the term of this patent is extended or adjusted under 35 U.S.C. 154(b) by 0 days.

(21) Appl. No.: 10/615,706

(22) Filed: Jul. 8, 2003

(51) Int. Cl.[7] ..... A01H 5/00
(52) U.S. Cl. ..... Plt./102
(58) Field of Search ..... Plt./102

*Primary Examiner*—Bruce R. Campell
*Assistant Examiner*—Annette H Para
(74) *Attorney, Agent, or Firm*—Klarquist Sparkman LLP

(57) ABSTRACT

Shrub rose plant having free and continuous flowering; unusual orange-red blooms, paling to salmon-pink; rosette-shaped flowers with outer petals reflexing a little; and pleasing tea fragrance with a hint of lemon.

1 Drawing Sheet

Genus and species: *Rosa hybrida.*
Variety denomination: 'AUSJUMP'.

ORIGIN OF THE INVENTION

The present invention relates to a new and distinct variety of a shrub rose plant named 'AUSjump' which was originated by me by crossing an unnamed seedling with the variety 'AUSgold', U.S. Plant Pat. No. 8,688.

BACKGROUND OF THE INVENTION

The primary objective of this breeding was to produce a new rose variety having a very free flowering and healthy plant, with orange-red flowers of a rosette shape, and good fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Unusual orange-red blooms, paling to salmon-pink.
2. Rosette-shaped flowers, outer petals reflexing a little.
3. Pleasing tea fragrance with a hint of lemon.
4. Free and continuous flowering.

Asexual reproduction of this new variety by budding, as performed at Albrighton, England, shows that the foregoing and all other characteristics and distinctions come true to form and are established and transmitted through succeeding propagations.

Comparison with Parents

'AUSgold' (Golden Celebration) has large, cupped, golden-yellow flowers on a medium shrub compared with the orange-red blooms of AUSjump. The seedling parent has deep pink flowers and grows to 240 cm, about thrice the height of AUSjump.

Comparison with Similar Variety

'AUSlot' (U.S. Plant Pat. No. 11,422) has rosette-shaped blooms that are light red in color, whereas 'AUSjump' has orange-red blooms. 'AUSjump' also has a hint of lemon in its fragrance.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling. (Unpatented).
*Pollen parent.*—'AUSgold' (U.S. Plant Pat. No. 8,688).

FLOWER

Observations made from plants commencing at one year of age grown in a garden environment at Albrighton, England.

Blooming habit: Continuous.

Bud:
*Size.*—About 4 cm long and 2.2 cm in diameter when the petals start to unfurl.
*Form.*—The bud form is pointed ovoid.
*Color.*—When sepals first divide, bud color is Yellow-Green Group 144A. When half blown, the upper sides of the petals are Red Group 52C; and the lower sides of the petals are Yellow-Orange Group 22D.
*Sepals.*—Color: Upper surface: Yellow-Orange Group 14B. Lower surface: Yellow-Orange Group 14B. Length: 2.7 cm. Width: 0.8 cm. Shape: Pointed. Surface texture: Hairy edges. Upper surface: Very hairy. Lower surface: Smooth. There are three lightly appendaged sepals. These are three unappendaged sepals with hairy edges.

*Receptacle.*—Color: Yellow-Green Group 144B. Shape: Pitcher. Size: Medium, about 1.1 cm long× 0.8 cm wide. Surface: Smooth.

*Peduncle.*—Surface: Smooth. Color: Yellow-Green Group 144B. Strength: Stiff.

Bloom:

*Size.*—Medium. Average open diameter is about 5.5 cm.

*Borne.*—Several together in flat clusters.

*Stems.*—Strength: Normal. Average length is about 85 cm with a diameter of 0.5 cm.

*Form.*—When first open: Flat. Permanence: Outer petals curl back.

*Petalage.*—Number of petals under normal conditions: 68.

*Color.*—The upper sides of the petals are Red Group 54B at the outer part and Red Group 54A towards the base. The reverse sides of the petals are Red Group 54B at the outer part and Yellow-Orange Group 19B towards the base. The base of each petal is Yellow Group 9B. The major color on the upper side is Red Group 54A.

*Variegations.*—None.

*Discoloration.*—The general tonality at the end of the first day: Red Group 52B. At the end of the third day: Fading to Red Group 54C.

*Fragrance.*—Moderate. Character of fragrance: Tea, with a hint of lemon.

Petals:

*Texture.*—Thick and leathery.

*Size.*—33 mm wide by 36 mm long.

*Shape.*—Round.

*Surfaces.*—Smooth.

*Margin.*—Reflexing and undulating. Apex Shape: Round. Base Shape: Pointed.

*Form.*—Edges slightly quilled.

*Arrangement.*—Quartered.

*Petaloids.*—Number: 14 Color: Greyed-Red Group 180D with spot of Yellow Group 10C at base.

*Persistence.*—Petals hang on and dry.

*Lastingness.*—On the plant: Fair (about 4 days). As a cut flower: Fair (about 4 days).

Reproductive parts:

*Stamens.*—Number: 25. Length: 0.5 cm. Anthers: Length: 0.1 cm. Color: Yellow-Orange Group 14B. Arrangement: Tucked in calyx. Filaments: Color: Green-Yellow Group 1C. Length: 0.5 cm. Pollen: Color: Yellow Group 9C.

*Pistils.*—Number: 20. Length: 0.6 cm. Styles: Color: Yellow Group 3C. Length: 0.8 cm. Stigmas: Color: Yellow Group 6B. Length: 0.1 cm.

*Hips.*—None observed.

PLANT

*Form.*—Shrub.

*Growth.*—Medium and branching.

*Age at maturity.*—2 years.

*Mature plant.*—Height: 70 cm. Width: 55 cm.

*Rootstock.*—Dr. Huey in the United States. *Rosa dumetorum laxa* for the observed plants in the United Kingdom.

Foliage: Number of leaflets on normal mid-stem leaves: 7 cm.

*Size.*—Medium. About 10 cm long×8.2 cm wide.

*Quantity.*—Normal.

*Color.*—New foliage: Upper side: Green Group 137C. Lower side: Green Group 138B. Old foliage: Upper side: Green Group 139A. Lower side: Green Group 138B.

Leaflets:

*Size.*—About 4.2 cm long×3.4 cm wide.

*Shape.*—Broadly oval and pointed oval.

*Base shape.*—Rounded.

*Apex shape.*—Acuminate.

*Texture.*—Leathery and smooth.

*Edge.*—Serrated.

*Serrations.*—Small.

*Petiole.*—Color: Yellow-Green Group 146D.

*Petiole rachis.*—Color: Yellow-Green Group 146D. Underside: Smooth.

*Auricle shape.*—Long point.

*Stipules.*—Length: 1.5 cm and serrated.

*Disease resistance.*—Resistant to mildew, blackspot, and rust under normal growing conditions.

*Pest persistence.*—Not tested.

*Vein color.*—Yellow-Green Group 146B.

*Venation pattern.*—Branching.

Wood:

*New wood.*—Color: Yellow Green Group 144B with blush of Greyed-Orange Group 176C. Bark: Smooth.

*Old wood.*—Color: Green Group 137D. Bark: Smooth.

Prickles:

*Quantity.*—On main canes from base: Ordinary. (20 per 46 cm). On laterals from main canes: Ordinary. (15 per 30 cm).

*Form.*—Hooked downward.

*Length.*—0.6 cm.

*Color when young.*—Red Group 42B.

*Color when mature.*—Red Group 50A.

Small prickles:

*Quantity.*—On main stalks: Few. On laterals: Few.

*Color.*—When young: Red Group 45B. When mature: Red Group 39B.

Winter hardiness: Not tested.

I claim:

1. A new and distinct variety of rose plant of the shrub class, substantially as herein shown and described, characterized particularly by its free and continuous flowering; unusual orange-red blooms, paling to salmon-pink; rosette-shaped flowers with outer petals reflexing a little; and pleasing tea fragrance with a hint of lemon.

* * * * *

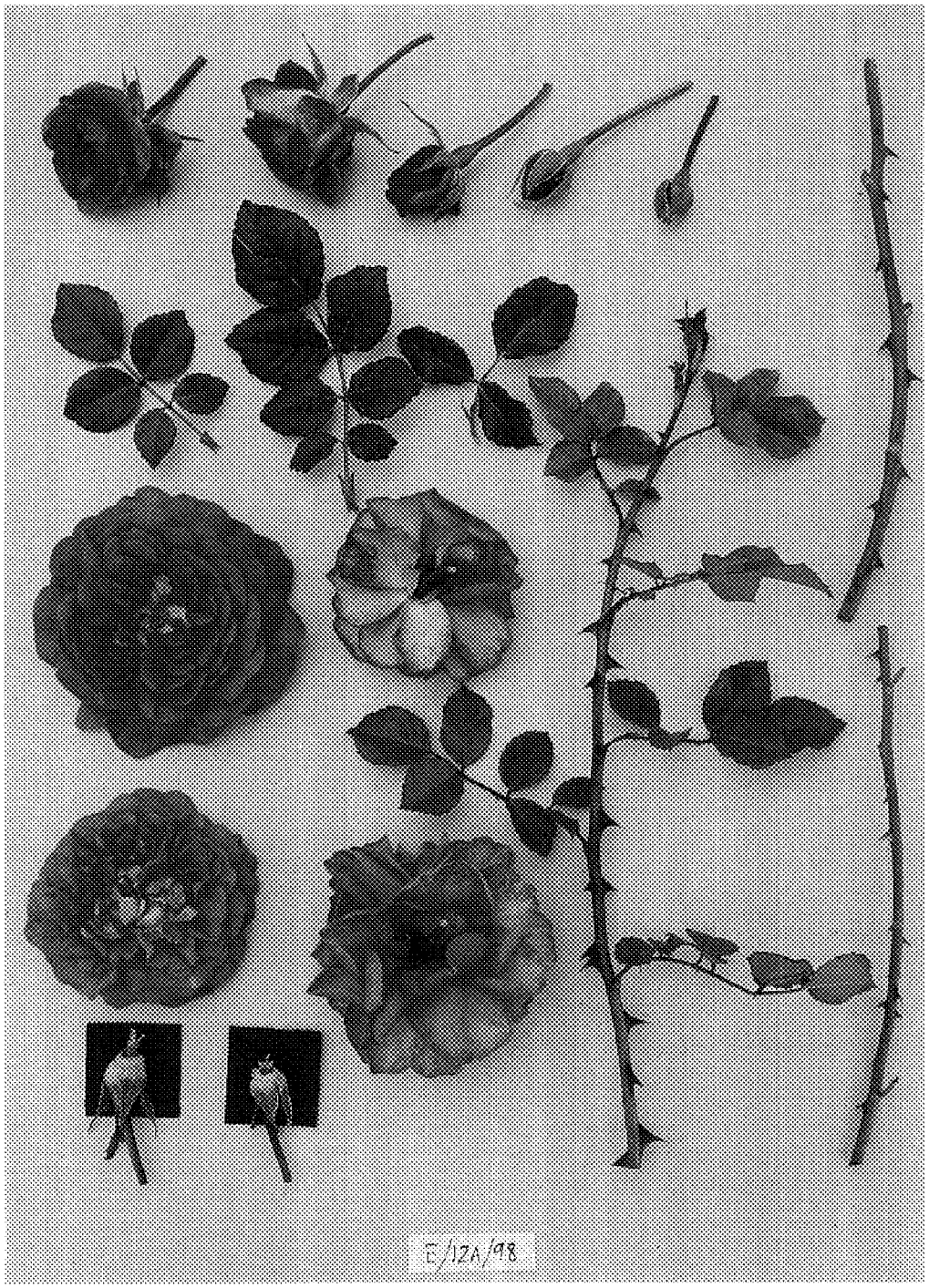
E/12A/98